US008673293B2

(12) United States Patent
Martin et al.

(10) Patent No.: US 8,673,293 B2
(45) Date of Patent: Mar. 18, 2014

(54) USE OF MODIFIED CELLS FOR THE TREATMENT OF MULTIPLE SCLEROSIS

(75) Inventors: Roland Martin, Hamburg (DE); Andreas Lutterotti, Mils (AT); Stephen Miller, Oak Park, IL (US)

(73) Assignee: Universitat Zurich, Zurich (CH)

(*) Notice: Subject to any disclaimer, the term of this patent is extended or adjusted under 35 U.S.C. 154(b) by 604 days.

(21) Appl. No.: 12/740,502

(22) PCT Filed: Oct. 31, 2008

(86) PCT No.: PCT/EP2008/009204
§ 371 (c)(1),
(2), (4) Date: Oct. 13, 2010

(87) PCT Pub. No.: WO2009/056332
PCT Pub. Date: May 7, 2009

(65) Prior Publication Data
US 2011/0033426 A1  Feb. 10, 2011

(30) Foreign Application Priority Data
Oct. 31, 2007 (EM) .................................. 07075952

(51) Int. Cl.
| | | |
|---|---|---|
| *A61K 35/14* | (2006.01) | |
| *A61K 35/18* | (2006.01) | |
| *A61K 39/385* | (2006.01) | |
| *A61P 25/00* | (2006.01) | |
| *A61K 38/01* | (2006.01) | |
| *A61K 38/10* | (2006.01) | |
| *A61K 38/17* | (2006.01) | |
| *A61P 25/28* | (2006.01) | |

(52) U.S. Cl.
USPC .................... 424/93.7; 424/93.71; 424/93.73; 424/93.1; 424/529; 424/533; 424/534; 424/184.1; 424/185.1; 424/193.1; 424/194.1; 514/1; 514/1.1; 514/17.7; 514/17.9

(58) Field of Classification Search
None
See application file for complete search history.

(56) References Cited

FOREIGN PATENT DOCUMENTS

WO   PCT2008009204 R   3/2009

OTHER PUBLICATIONS

Bielekova B et al. "Expansion and Functional Relevance of High-Avidity Myelin-Specific CD4 <+> T Cells in Multiple Sclerosis." (Journal of Immunology), Mar. 15, 2004, 3893-3904, 172: 6.
Kohm, Adam P et al. "Targeting the TCR: T-cell receptor and peptide-specific tolerance-based strategies for restoring self-tolerance in CNS autoimmune disease." (International Reviews of Immunology), Sep. 2005, 361-392, 24: 5.
Martin R et al. "Future therapeutic options for multiple sclerosis." (Aktuelle Neurologie), May 2008, 169-176, 35: 4.
Miller, Stephen D et al. "Antigen-specific tolerance strategies for the prevention of treatment of autoimmune disease." (Nature Reviews Immunology), Sep. 2007, 665-677, 7: 9.
Ponomarenko Natalia A et al. "Autoantibodies to myelin basic protein catalyze site-specific degradation of their antigen." (Proceedings of the National Academy of Science of the United States of America), Jan. 2006, 281-286, 103: 2.
Smith et al. "Multi-peptide coupled-cell tolerance ameliorates ongoing relapsing EAE associated with multiple pathogenic autoreactivities." (Journal of Autoimmunity), Feb. 6, 2007, 218-231, 27: 4.
Sorbera L. A. "MBP-8298. Agent for Multiple Sclerosis." (Drugs of the Future), Oct. 2006, 864-866, 31: 10.
Sospedra, Mireia et al. "Immunology of multiple sclerosis." (Annual Review of Immunology), 2005, 683-747, 23.
Turley, Danielle M et al. "Peripheral tolerance induction using ethylenecarbodiimide-fixed APCs uses both direct and indirect mechanisms of antigen presentation for prevention of experimental autoimmune encephalomyelitis." (Journal of Autoimmunology), Feb. 2007, 2212-2220, 178: 4.
Vandenbark, Arthur A et al. "Differential susceptibility of human Th1 versus Th2 cells to induction of anergy and apoptosis by EDCI/antigen-coupled antigen-presenting cells." (International Immunology), Jan. 2000, 57-66, 12: 1.
Warren K G et al. "Intravenous synthetic peptide MBP8298 delayed disease progression in an HLA Class II-defined cohort of patients with progressive multiple sclerosis: results of a 24-month double-blind placebo-controlled clinical trial and 5 years of follow-up treatment." (European Journal of Neurology), Aug. 2006, 887-895, 13:8.
KK Tsilidis et al. "Evaluation of Excess Significance Bias in Animal Studies of Neurological Diseases." PLoS Biol. Jul. 2013;11(7):e1001609; Epub Jul. 16, 2013, pp. 1-10.
J Mestas et al. "Of mice and not men: differences between mouse and human immunology." J Immunol. Mar. 1, 2004;172(5):2731-8.
JM Chase "The shadow of bias." PLoS Biol. Jul. 2013;11(7):e1001608; Epub Jul. 16, 2013, pp. 1-2.
A Lutterotti et al. "Antigen-specific tolerance by autologous myelin peptide-coupled cells: a phase 1 trial in multiple sclerosis." Sci Transl Med. 5(188); Jun. 5, 2013, pp. 1-11.

*Primary Examiner* — Chris R Tate
*Assistant Examiner* — Aaron J Kosar
(74) *Attorney, Agent, or Firm* — Millen, White, Zelano & Branigan, P.C.

(57) ABSTRACT

The present invention describes blood cells chemically coupled with immunodominant myelin peptides and their use in the treatment of Multiple Sclerosis.

14 Claims, 8 Drawing Sheets

Figure 3:
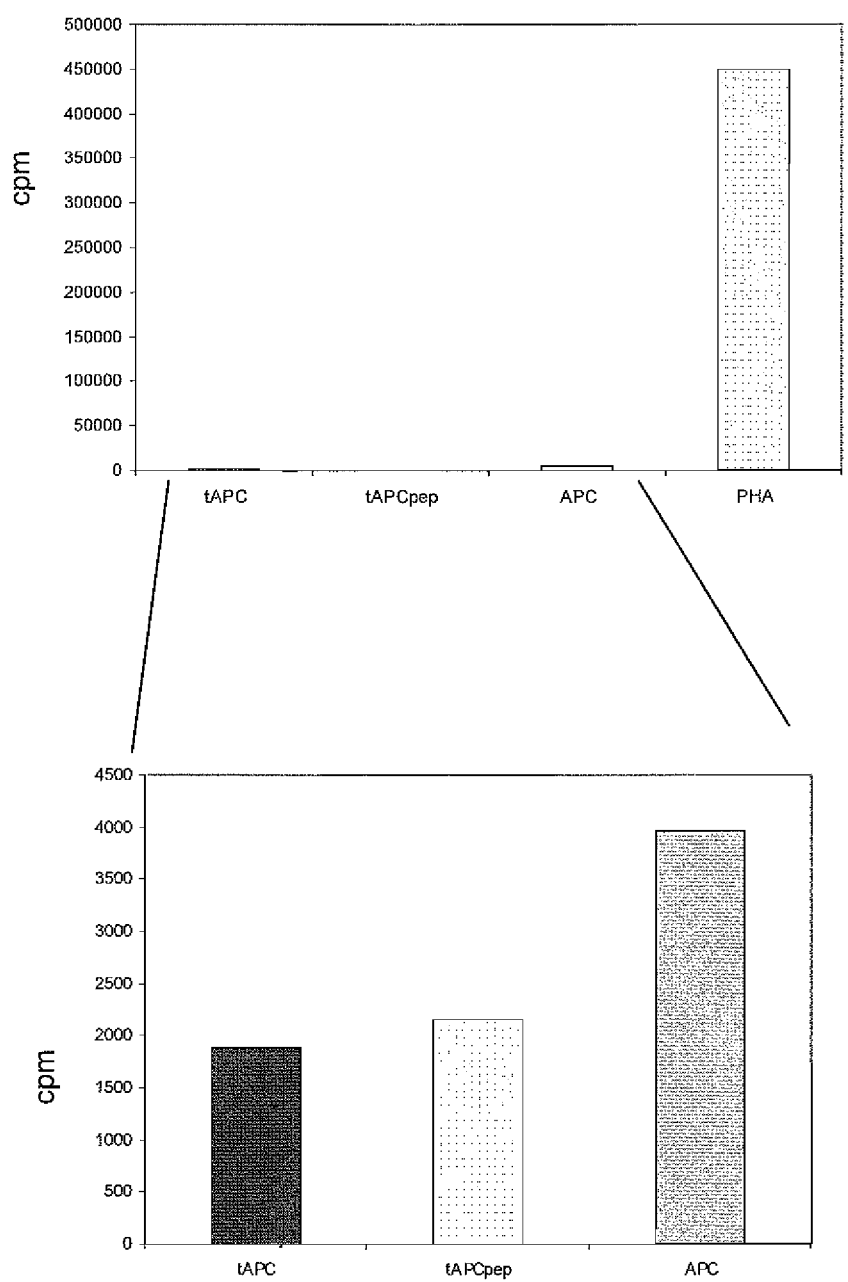

Fig. 1
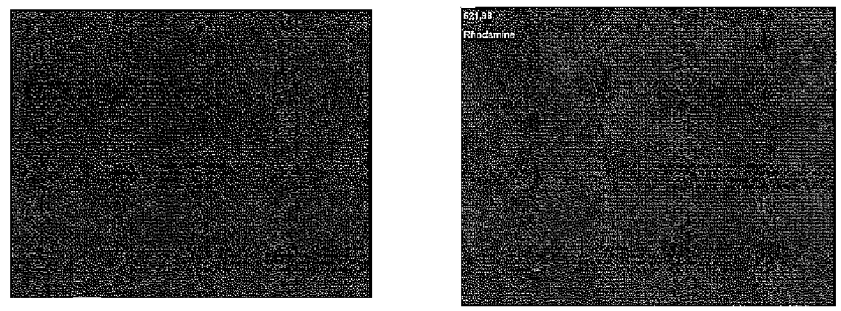
Streptavidin Cy3
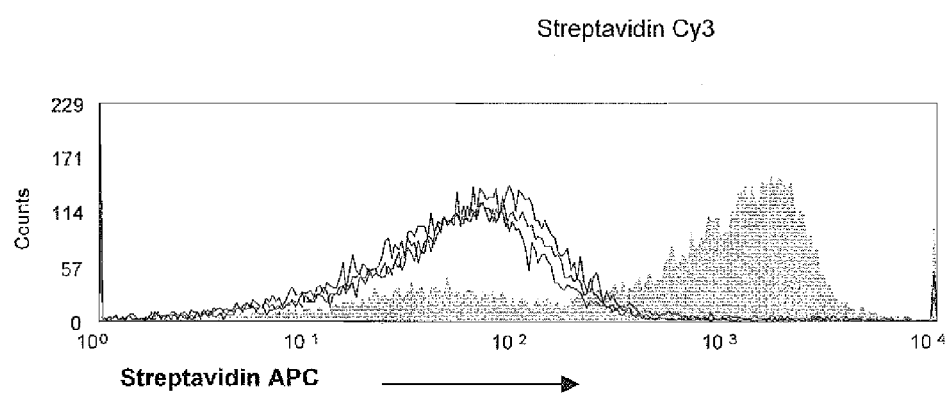
Streptavidin APC
|  | biotinPLP130-154 | EDC |
|---|---|---|
| 1 open histogram |  |  |
| 2 open histogram | − | + |
| 3 open histogram | + | − |
| 4 filled histogram | + | + |
Cell were pulsed in-vitro in the presence or absence of either biotinPLP, EDC or both. Only in the presence of both EDC and biotinPLP we detect the peptide on the surface of cells

Fig.: 2
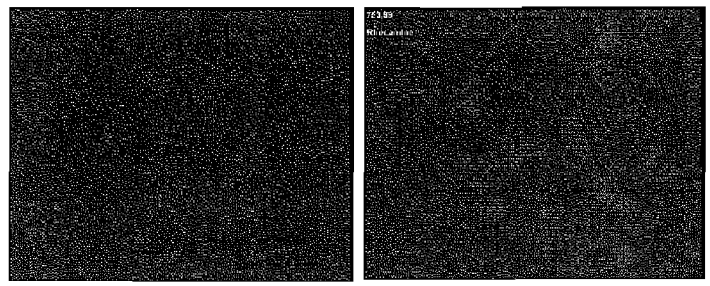
Streptavidin Cy3
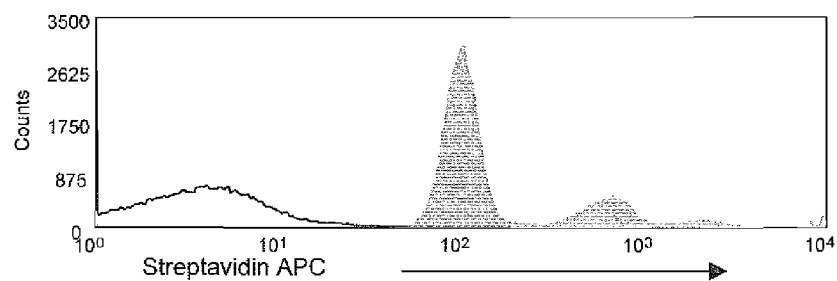
Streptavidin APC
Open histogram    PBMC after lysis, before coupling reaction
Filled histogram   Product (PBMC after coupling reaction)
Biotin peptide is efficiently bound to the cells during the manufacture process in bags.

Cytokine response in PBMC pre-activated with PHA and cultured in the presence of APC, tAPC or tAPCpep.

SEQUENCE LISTING

<160> NUMBER OF SEQ ID NOS: 9

<210> SEQ ID NO 1
<211> LENGTH: 20
<212> TYPE: PRT
<213> ORGANISM: Homo sapiens

<400> SEQUENCE: 1

Lys Tyr Leu Ala Thr Ala Ser Thr Met Asp His Ala Arg His Gly Phe

```
                1               5                  10                  15
Leu Pro Arg His
              20

<210> SEQ ID NO 2
<211> LENGTH: 17
<212> TYPE: PRT
<213> ORGANISM: Homo sapiens

<400> SEQUENCE: 2

Glu Asn Pro Val Val His Phe Phe Lys Asn Ile Val Thr Pro Arg Thr
1               5                  10                  15

Pro

<210> SEQ ID NO 3
<211> LENGTH: 19
<212> TYPE: PRT
<213> ORGANISM: Homo sapiens

<400> SEQUENCE: 3

Leu Ser Arg Phe Ser Trp Gly Ala Glu Gly Gln Arg Pro Gly Phe Gly
1               5                  10                  15

Tyr Gly Gly

<210> SEQ ID NO 4
<211> LENGTH: 25
<212> TYPE: PRT
<213> ORGANISM: Homo sapiens

<400> SEQUENCE: 4

Ala Gln Gly Thr Leu Ser Lys Ile Phe Lys Leu Gly Gly Arg Asp Ser
1               5                  10                  15

Arg Ser Gly Ser Pro Met Ala Arg Arg
              20                  25

<210> SEQ ID NO 5
<211> LENGTH: 16
<212> TYPE: PRT
<213> ORGANISM: Homo sapiens

<400> SEQUENCE: 5

His Cys Leu Gly Lys Trp Leu Gly His Pro Asp Lys Phe Val Gly Ile
1               5                  10                  15

<210> SEQ ID NO 6
<211> LENGTH: 20
<212> TYPE: PRT
<213> ORGANISM: Homo sapiens

<400> SEQUENCE: 6

Gly Gln Phe Arg Val Ile Gly Pro Arg His Pro Ile Arg Ala Leu Val
1               5                  10                  15

Gly Asp Glu Val
              20

<210> SEQ ID NO 7
<211> LENGTH: 21
<212> TYPE: PRT
<213> ORGANISM: Homo sapiens

<400> SEQUENCE: 7

Met Glu Val Gly Trp Tyr Arg Pro Pro Phe Ser Arg Val Val His Leu
1               5                  10                  15
```

```
Tyr Arg Asn Gly Lys
            20

<210> SEQ ID NO 8
<211> LENGTH: 17
<212> TYPE: PRT
<213> ORGANISM: Homo sapiens

<400> SEQUENCE: 8

Asp Glu Asn Pro Val Val His Phe Phe Lys Asn Ile Val Thr Pro Arg
1               5                   10                  15

Thr

<210> SEQ ID NO 9
<211> LENGTH: 12
<212> TYPE: PRT
<213> ORGANISM: Homo sapiens

<400> SEQUENCE: 9

Pro Val Val His Phe Phe Lys Asn Ile Val Thr Pro
1               5                   10
```

USE OF MODIFIED CELLS FOR THE TREATMENT OF MULTIPLE SCLEROSIS

SEQUENCE LISTING

The instant application contains a Sequence Listing which has been submitted in ASCII format via EFS-Web and is hereby incorporated by reference in its entirety. Said ASCII copy, created on Oct. 1, 2010, is named JS0079.txt and is 2,398 bytes in size.

Multiple sclerosis (MS) is a devastating autoimmune inflammatory disease of the brain and spinal cord mainly affecting young adults.

Multiple sclerosis (MS) is the most frequent debilitating neurological disease of young adults in Europe (prevalence 60-200/100,000, incidence 2-4/100,000), with half of patients needing a walking aid 10-15 years from onset of the disease. MS ranks second only to trauma in the age group of young adults with respect to socio-economic costs. The symptoms of MS vary, depending on the location of lesions within the CNS, including focal weakness, sensory deficits, double vision, loss of vision; imbalance, fatigue, urinary and bowel dysfunction, sexual impairment and cognitive decline. In most patients the disease starts with a relapsing-remitting disease course (RR-MS), which is followed by a secondary progressive deterioration usually beginning about ten years after disease onset (SP-MS). The etiology is unknown, but it is well accepted that the damage in the central nervous system (CNS) results from an autoimmune attack against (auto)antigens within the myelin sheath. Currently approved therapies for MS involve various antigen-nonspecific immunomodulating or immunosuppressive strategies, which are only partially effective in that they prevent 30%-50% of relapses. Preventing progression of disability has not been consistently demonstrated for these therapies, yet. However all therapeutics need to be injected for long periods of time and are associated with considerable side effects. Particularly in a chronic disease as MS, therapy should aim to specifically delete or functionally inhibit pathogenic autoreactive cells without altering the "normal" immune system. This is of importance because global immunomodulation and/or immunosuppression come at the cost of inhibiting beneficial regulatory cells and immune cells that might serve protective functions. Thus the ideal treatment would be early intervention using an antigen-specific tolerance protocol that selectively targets both activated and naïve autoreactive T cells specific for multiple potential encephalitogenic epitopes that perpetuate the disease.

The mechanisms responsible for tissue damage in MS involve the activation of self-reactive T lymphocytes which attack proteins in the myelin sheath. Current therapies for MS inhibit the autoimmune response in a nonspecific manner, are only moderately effective and can have significant side effects. Based on success in pre-clinical experiments in animal models of MS, we have invented a new therapeutic strategy, which will specifically target only the autoreactive CD4+ T lymphocytes. Tolerance will be induced by a single administration of blood cells, in particular red blood cells, more particularly peripheral blood mononuclear cells chemically coupled with a mixture of synthetic myelin antigens to which T cell responses are demonstrable in early MS patients. The therapy is exquisitely antigen-specific and renders autoreactive T cells non-functional or anergic.

The induction of tolerance to target autoantigens is a highly important therapeutic goal in autoimmune diseases. It offers the opportunity to attenuate specifically the pathogenic autoimmune response in an effective way with few side effects. To achieve this goal we adopt a very promising tolerization strategy that employs autologous peptide-pulsed, fixed, antigen presenting cells as tolerogen. This therapy has proven excellent efficacy in animal models of MS and different T cell-mediated autoimmune diseases.

The therapy is based on systemic administration of blood cells chemically coupled with a cocktail of peptides containing at least five of eight immunodominant myelin peptides (MBP 13-32, MBP 83-99, MBP 111-129, MBP 146-170, PLP 139-154, MOG 1-20, MOG 35-55 and MBP 82-98), to which T cell responses are demonstrable in early RR-MS patients. Preferred is the use of six, seven or eight of the named immunodominant myelin peptides (MBP 13-32, MBP 83-99, MBP 111-129, MBP 146-170, PLP 139-154, MOG 1-20, MOG 35-55 and MBP 82-98).

The blood cells may be autologous blood cells or may be allogeneic blood cells. Preferred blood cells are red blood cells. More preferred are peripheral blood mononuclear cells (PBMCs). The preferred route for systemic administration is i.v. administration.

A preferred aspect of the invention is therefore a therapy based on systemic administration of autologous peripheral blood mononuclear cells chemically coupled with a cocktail containing at least five of eight immunodominant myelin peptides (MBP 13-32, MBP 83-99, MBP 111-129, MBP 146-170, PLP 139-154, MOG 1-20, MOG 35-55 and MBP 82-98), to which T cell responses are demonstrable in early RR-MS patients. Preferred is the use of six, seven or eight of the named immunodominant myelin peptides (MBP 13-32, MBP 83-99, MBP 111-129, MBP 146-170, PLP 139-154, MOG 1-20, MOG 35-55 and MBP 82-98).

Even more preferred is the use of one of a cocktail of peptides, wherein the cocktail is selected from:
a) MBP 13-32, MBP 83-99, MBP 111-129, MBP 146-170, PLP 139-154, MOG 1-20 and MOG 35-55
b) MBP 13-32, MBP 82-98, MBP 111-129, MBP 146-170, PLP 139-154, MOG 1-20 and MOG 35-55
c) MBP 13-32, MBP 83-99, MBP 111-129, MBP 146-170, PLP 139-154, MOG 1-20, MOG 35-55 and MBP 82-98
d) MBP 13-32, MBP 111-129, MBP 146-170, PLP 139-154, MOG 1-20 and MOG 35-55.

Most preferred in this aspect of the invention is the use of the cocktail consisting of the following seven peptides MBP 13-32, MBP 83-99, MBP 111-129, MBP 146-170, PLP 139-154, MOG 1-20 and MOG 35-55.

The preferred route for systemic administration is i.v. administration.

Another preferred aspect of the invention is therefore a therapy based on systemic administration of allogeneic peripheral blood mononuclear cells chemically coupled with a cocktail containing at least five of eight immunodominant myelin peptides (MBP 13-32, MBP 83-99, MBP 111-129, MBP 146-170, PLP 139-154, MOG 1-20, MOG 35-55 and MBP 82-98), to which T cell responses are demonstrable in early RR-MS patients. Preferred is the use of six, seven or eight of the named immunodominant myelin peptides (MBP 13-32, MBP 83-99, MBP 111-129, MBP 146-170, PLP 139-154, MOG 1-20, MOG 35-55 and MBP 82-98). Most preferred in this aspect is the use of the cocktail consisting of the following seven peptides MBP 13-32, MBP 83-99, MBP 111-129, MBP 146-170, PLP 139-154, MOG 1-20 and MOG 35-55.

The preferred route for systemic administration is i.v. administration.

Extensive immunological studies, including human in-vitro studies and animal in-vitro and in vivo studies do document the safety, efficacy and in vivo mechanisms of action of the regimens described above.

Aspects of the invention are therefore (amongst others)

1.) A blood cell chemically coupled with at least five of the following eight immunodominant myelin peptides:
MBP 13-32, MBP 83-99, MBP 111-129, MBP 146-170, PLP 139-154, MOG 1-20, MOG 35-55 and MBP 82-98.

2) A blood cell chemically coupled with a cocktail containing six, seven or eight of the following eight immunodominant myelin peptides:
MBP 13-32, MBP 83-99, MBP 111-129, MBP 146-170, PLP 139-154, MOG 1-20, MOG 35-55 and MBP 82-98.

3) A blood cell chemically coupled with a cocktail of peptides, wherein the cocktail is selected from
a) MBP 13-32, MBP 83-99, MBP 111-129, MBP 146-170, PLP 139-154, MOG 1-20 and MOG 35-55
b) MBP 13-32, MBP 82-98, MBP 111-129, MBP 146-170, PLP 139-154, MOG 1-20 and MOG 35-55
c) MBP 13-32, MBP 83-99, MBP 111-129, MBP 146-170, PLP 139-154, MOG 1-20, MOG 35-55 and MBP 82-98
d) MBP 13-32, MBP 111-129, MBP 146-170, PLP 139-154, MOG 1-20

4) A red blood cell chemically coupled with at least five of the following eight immunodominant myelin peptides:
MBP 13-32, MBP 83-99, MBP 111-129, MBP 146-170, PLP 139-154, MOG 1-20, MOG 35-55 and MBP 82-98.

5) A red blood cell chemically coupled with a cocktail containing six, seven or eight of the following eight immunodominant myelin peptides:
MBP 13-32, MBP 83-99, MBP 111-129, MBP 146-170, PLP 139-154, MOG 1-20, MOG 35-55 and MBP 82-98.

6) A red blood cell chemically coupled with a cocktail a cocktail of peptides, wherein the cocktail is selected from
a) MBP 13-32, MBP 83-99, MBP 111-129, MBP 146-170, PLP 139-154, MOG 1-20 and MOG 35-55
b) MBP 13-32, MBP 82-98, MBP 111-129, MBP 146-170, PLP 139-154, MOG 1-20 and MOG 35-55
c) MBP 13-32, MBP 83-99, MBP 111-129, MBP 146-170, PLP 139-154, MOG 1-20, MOG 35-55 and MBP 82-98
d) MBP 13-32, MBP 111-129, MBP 146-170, PLP 139-154, MOG 1-20 and MOG 35-55.

7) A peripheral blood mononuclear cell chemically coupled with at least five of the following eight immunodominant myelin peptides:
MBP 13-32, MBP 83-99, MBP 111-129, MBP 146-170, PLP 139-154, MOG 1-20, MOG 35-55 and MBP 82-98.

8) A peripheral blood mononuclear cell chemically coupled with a cocktail containing six, seven or eight of the following eight immunodominant myelin peptides:
MBP 13-32, MBP 83-99, MBP 111-129, MBP 146-170, PLP 139-154, MOG 1-20, MOG 35-55 and MBP 82-98.

9) A peripheral blood mononuclear cell chemically coupled with a cocktail of peptides, wherein the cocktail is selected from
a) MBP 13-32, MBP 83-99, MBP 111-129, MBP 146-170, PLP 139-154, MOG 1-20 and MOG 35-55
b) MBP 13-32, MBP 82-98, MBP 111-129, MBP 146-170, PLP 139-154, MOG 1-20 and MOG 35-55
c) MBP 13-32, MBP 83-99, MBP 111-129, MBP 146-170, PLP 139-154, MOG 1-20, MOG 35-55 and MBP 82-98
d) MBP 13-32, MBP 111-129, MBP 146-170, PLP 139-154, MOG 1-20 and MOG 35-55.

It has to be understood that in any of the aspects 1-9 described above the blood cells may be autologous or allogeneic.

In an animal model of MS, experimental autoimmune encephalomyelitis (EAE), this protocol has shown dramatic therapeutic efficacy on clinical and pathological signs of disease. It not only silences the immune response against the major autoantigen, but also prevents epitope spreading to other myelin peptides within the same protein (intramolecularly) and also additional myelin proteins (intermolecularly), which represents an important advantage over other therapies. We expect that treatment will decrease the average number of monthly contrast-enhancing MRI lesions by 50% or greater and reduce the number, change the phenotype of myelin peptide-specific T cells from a pro-inflammatory Th1/Th17 to an anti-inflammatory Th2-like type and/or render autoreactive T cells anergic.

Advantages of the protocol are: 1. Tolerance is exquisitely antigen-specific and therefore will not alter the normal immune response as do current immunosuppressive regimens. 2. From preclinical studies we note that in most cases a single intravenous infusion of peptide-pulsed peripheral blood mononuclear cells (PBMC) will induce long-term amelioration, which is a substantial improvement compared to all current therapies.

If needed, patients may be treated more than once in their life-time (they may be re-treated as needed e.g. on a yearly basis). 3. Tolerance is inducible in both naïve and activated Th1 cells. It is considered safer and more effective than tolerance induced by peripheral administration of soluble peptide or DNA vaccination with myelin peptide, which are both currently in phase II and -III clinical testing.

MS and role of T cells: Current evidence suggests CD4+ autoreactive T cells as a central factor for the autoimmune pathogenesis of MS probably relevant not only for the induction and maintenance of the autoimmune response, but also during tissue damage (Sospedra and Martin 2005, Annu. Rev. Immunol. 23:683). The frequency of activated CD4+ T cells reactive to main constituents of the myelin sheath, such as myelin basic protein (MBP), proteolipid protein (PLP) and myelin oligodendrocyte glycoprotein (MOG) is increased in MS patients. Recently we demonstrated that high avidity myelin-specific T cells, which derive from the memory T cell pool and preferentially express a Th1 cytokine phenotype, are clearly more frequent in MS patients than in controls (Bielekova et al. 2004, J. Immunol. 172:3893). Due to their pathogenetic involvement CD4+ T cells are one logical target for therapeutic interventions. Tolerization by peptide-pulsed, fixed APC in the animal model of MS: Many pathological characteristics of human MS are reflected in the situation of EAE, a paradigmatic model of Th1/Th17 cell-driven autoimmune disease. Studies in relapsing EAE (R-EAE) in the SJL mouse have clearly shown that chronic demyelination involves the activation of T cell responses to multiple endogenous antigens arising via epitope spreading (Vanderlugt and Miller 2002, Nat. Rev. Immunol 2:85). Unresponsiveness of T cells can be induced when antigen presenting cells (APC) pulsed with antigenic peptide are treated with the cross linker 1-ethyl-3-(3-dimethylaminopropyl)-carbodiimide (ECDI).

A still further aspect of the invention is a peripheral blood mononuclear cell as described above in which the chemical coupling is achieved by 1-ethyl-3-(3-dimethylaminopropyl)-carbodiimide (ECDI).

Preclinical experiments have proven that a single i.v. injection of naïve murine splenocytes pulsed with a mixture of encephalitogenic myelin peptides and fixed with the cross linker ECDI is highly efficient in inducing peptide-specific tolerance in vivo. In EAE this protocol not only prevented animals from disease but even effectively reduced the onset and severity of all subsequent relapses when given after disease induction, indicating that specific tolerance can down regulate an ongoing autoimmune response (Kohm and Miller 2005, Int. Rev. Immunol. 24:361). More relevant to the treatment of MS, studies in EAE have shown that tolerance can be simultaneously induced to multiple epitopes using a cocktail of encephalitogenic myelin peptides, thus providing the capacity to target autoreactive T cells with multiple specifities. This regimen of antigen-specific peripheral tolerance is superior to tolerance induction by oral, subcutaneous or intraperitoneal administration of antigen and has also proven to be safe and effective in other experimental models of different T cell driven autoimmune diseases and in allograft rejection. Tolerization of human T cells by autologous antigen-coupled APCs treated with ECDI is effective in vitro as shown by failure of tolerized T cells to proliferate or to produce Th1 cytokines and a decreased expression of costimulatory molecules on these cells (Vandenbark et al. 2000, Int. Immunol. 12:57). There is evidence that at least two distinct mechanisms are involved in the induction of antigen specific tolerance by this regime. 1) Direct tolerance where Th1 clones encountering nominal antigen/MHC complexes on chemically-fixed APCs were energized as a result of failure to receive adequate CD28-mediated costimulation (Jenkins and Schwartz. 1987, J. Exp. Med. 165:302) and 2) an indirect mechanism (cross tolerance) where tolerance is induced by reprocessing and re-presentation of antigens by host APCs (Turley and Miller, 2007, J. Immunol 178:2212). Treatment of cells with ECDI induces apoptosis in a substantial percentage of treated cells. Thus an indirect mechanism that involves fixed APC undergoing apoptosis, which are then processed and represented by host APC, is likely. This is further supported by effective induction of tolerance in MHC deficient and allogeneic mice. In-vitro bone marrow derived dendritic cells effectively phagocyte and process antigen pulsed, fixed APC. Choice of Peptides for Tolerization: Based on the rationale that T cells that recognize myelin peptides with high functional avidity might be most relevant for the autoimmune process in MS, we have recently focused on high avidity myelin-specific T cells and employed 16 myelin peptides derived from MBP, PLP, MOG and CNPase (Bielekova at al. 2004, J. Immunol. 172:3893). In summary these studies showed the following: (1) high avidity myelin-specific T cells are clearly more frequent in MS patients than in controls; (2) most of these T cells are derived from the memory T cell pool, and (3) express a Th1 cytokine phenotype; (4) only myelin epitopes MBP 13-32, MBP 111-129, MBP 146-170, PLP 139-154, MOG 1-20 and MOG 35-55 contributed to the increased reactivity observed in MS patients and (5) each those peptides against which high avidity T cells are mainly directed, is predicted as a poor binder to the main MS-associated HLA-DR alleles, which indicates that myelin peptides that bind poorly to MS-associated DR alleles are less likely to induce negative selection in the thymus. It should be noted that MBP peptide 83-99 will be included because this peptide has been shown to be immunodominant in MS patients by many prior studies and a phase III trial with i.v. MBP 82-98 is currently under way.

Further aspects of the invention therefore include:
10) A pharmaceutical composition containing blood cells as described herein for systemic administration.
11) A pharmaceutical composition containing blood cells as described herein for i.v. administration.
12) A medical product containing at least one cell as described herein.
13) The use of cells as described herein for the manufacture of a medicament for the treatment of MS.
14) The use of cells as described herein for the manufacture of a medicament for the treatment of MS, characterized in that the cells are allogeneic cells.
15) The use of cells as described herein for the manufacture of a medicament for the treatment of MS, characterized in that the cells are autologous cells.
16) A method of treating patients suffering from MS by systemic administration of a pharmaceutical composition containing blood cells coupled with a cocktail of peptides as described herein.

Innovation

ETIMS is a cell-based tolerization therapy that involves autologous antigen-presenting cells pulsed with a specific set of myelin peptides in the presence of a chemical coupling agent. This therapy is in many aspects novel and unique. These include a) the use of a set of peptides that covers the immunodominant epitopes of those myelin proteins, which are targeted by the high-avidity autoimmune T cell response in MS, b) different from all other tolerization therapies, ETIMS was shown to prevent epitope spreading, i.e. the broadening of the autoimmune response to other target epitopes, c) based on extensive animal testing, ETIMS is expected to be safer and more effective than those tolerization therapies that are currently in clinical testing in MS, i.e. administration of a single soluble peptide intravenously by BioMS and intramuscular administration of a plasmid encoding a myelin peptide together with a Th2 cytokine by Bayhill Pharmaceuticals, d) we expect that only a single treatment is required, which represents a major advantage with respect to patient acceptance.

The specificity, lack of side effects, and single time administration are considered major advantages of this treatment.

The scientific strategy follows two major goals: 1. To establish the efficacy and safety of ETIMS as a tolerizing treatment in early MS, and 2. To establish the precise in vivo mechanism of action of ETIMS. These mechanistic studies will include the exploration of more selective cell populations for tolerization, e.g. immature dendritic cells, B cells, others, in order to improve both efficacy and our intellectual property position.

Ideally peptide specific immune tolerance should be achieved early in the inflammatory phase of the disease, where blockade of the autoreactive immune response can inhibit dissemination and propagation of the disease and irreversible disability can be prevented. Therefore the targeted patient group are relapsing-remitting MS patients early in the disease course or even patients presenting with a first clinical event suggestive of MS, i.e. clinically isolated syndromes (CIS). At this time point MS patients generally have a low grade of neurologic disability, which allows them to participate in all activities of daily life and work without significant compromise.

One further aspect of the invention is a medicinal product for human use (ETIMS) containing blood cells that have been pulsed with at least five of eight immunodominant myelin peptides (MBP 13-32, MBP 83-99, MBP 111-129, MBP 146-170, PLP 139-154, MOG 1-20, MOG 35-55 and MBP 82-98) and fixed with the cross-linker ECDI. Preferred blood cells are red blood cells, more preferred blood cells are peripheral blood mononuclear cells (PBMC). The blood cells may be autologous or allogeneic.

A preferred aspect of the invention is a medicinal product for human use (ETIMS) containing blood cells that have been pulsed with six, seven or eight of eight immunodominant myelin peptides (MBP 13-32, MBP 83-99, MBP 111-129, MBP 146-170, PLP 139-154, MOG 1-20, MOG 35-55 and MBP 82-98) and fixed with the cross-linker ECDI. Preferred blood cells are red blood cells, more preferred blood cells are peripheral blood mononuclear cells (PBMC). The blood cells may be autologous or allogeneic.

An even more preferred aspect of the invention is a medicinal product for human use (ETIMS) containing blood cells that have been pulsed with a cocktail of peptides according to claim 1, wherein the cocktail is selected from
 a) MBP 13-32, MBP 83-99, MBP 111-129, MBP 146-170, PLP 139-154, MOG 1-20 and MOG 35-55
 b) MBP 13-32, MBP 82-98, MBP 111-129, MBP 146-170, PLP 139-154, MOG 1-20 and MOG 35-55
 c) MBP 13-32, MBP 83-99, MBP 111-129, MBP 146-170, PLP 139-154, MOG 1-20, MOG 35-55 and MBP 82-98
 d) MBP 13-32, MBP 111-129, MBP 146-170, PLP 139-154, MOG 1-20 and MOG 35-55.
and fixed with the cross-linker ECDI. Preferred blood cells are red blood cells, more preferred blood cells are peripheral blood mononuclear cells (PBMC). The blood cells may be autologous or allogeneic.

The safety, preliminary efficacy and in vivo mechanisms of action of ETIMS in early relapsing remitting MS patients can be demonstrated in a clinical trial.

Manufacture Process:

The manufacturing process for the blood cells according to the invention is described below by way of example. It has to be understood that this description is not limiting in any way. An expert in the art is able to adapt the example to specific needs without any need to be inventive. The description below is in particular easily adaptable to other types of blood cells.

The excipients erythrocyte lysis buffer and peptide solution will be produced in advance and stored at <−20° C.

Peptide Solution

The peptide solution is prepared in the clean room (Category A) in the Department of Transfusion Medicine. First, 30 (±3) mg of each single peptide are weighed in and solved in 7.5 ml of water for injections (final concentration of peptide 4 mg/ml), respectively. Thereafter all peptides are pooled by transferring 5 ml of each single-peptide solution into a new tube and adding 5 ml of water for injections (total volume 40 ml) to obtain a final concentration of 0.5 mg/ml of each single peptide. Peptide-pool solution is aliquoted in 1.5 ml aliquots (20 aliquots) in sterile and endotoxin free NUNC Cryo Tube vials (NalgeNunc International) and stored at −20° C. until use. 5 ml of the Peptide-pool solution are transferred into a blood-bag containing 30 ml of water for injections for sterility testing. 5 ml are aliquoted at 1 ml and stored at −20° C. for later quality controls. Peptide-pool solutions have to pass sterility control before they can be used in the manufacture process. The identity and presence of each single peptide in the pool will be verified. The maximum storage time is 3 months.

At the day of manufacture of drug product, 1 ml of peptide-solution is transferred to a blood bag (P1459, Fresenius; see IMPD 2.1.P.3.5 *Filling of blood bags in clean room*). The procedure is done in the clean room (category A). The blood bag containing the peptide solution is stored at 4° C. until use.

Erythrocyte Lysis Buffer

The preparation of the erythrocyte lysis buffer is done in the clean room in the Department of Transfusion Medicine. Briefly, 4 g of Ammonium chloride EMPROVE® Ph Eur and 0.5 g of Potassium hydrogen carbonate EMPROVE® Ph Eur are solved in 50 ml of water for injection (Ph Eur). Using a 50 ml syringe 25 ml of the solved lysing buffer are transferred to a blood bag through a sterile filter (0.2 µm, Millipore). The blood bag is filled up to 200 ml with water for injection and stored at −20° C. until use. Two bags are filled. 50 ml of lysis buffer are transferred to a blood bag for sterility testing and 50 ml are preserved at −20° C. for later quality control. Erythrocyte lysis buffer solutions have to pass sterility control before they can be used in the manufacture process. The maximum storage time is three months.

CPD/Saline Washing Solution

At the day of the manufacture process a CPD bag (Compoflex, Fresenius) containing 63 ml of CPD will be filled up to 500 ml with sterile physiologic saline (NaCl 0.9%, Baxter) solution. Bags will be connected by TSCD. A balance (PC4000, Mettler) is used to control for weight (500 g). Two bags are produced. At the end of the manufacture process residual washing solution is tested for sterility.

EDC Solution

In the clean room (Cat. A) 200 mg EDC are solved in 2 ml of water for injection. Using a sterile syringe 1 ml is transferred to a blood bag (P1459, Fresenius). The blood bag with the EDC solution is stored at 4° C. until use. Residual EDC is tested for sterility.

Collection of PBMC and Plasma

At the day of blood collection $2.5-5\times10^9$ PBMC will be isolated from study-qualifying MS patients by standard leukapheresis, performed according to policies and procedures at the Department of Transfusion Medicine. For the collection of cells we use a standardized automatic program (AutoPBSC) on a Cobe Spectra apheresis machine (Cobe Spectra). The AutoPBSC processes 4500 ml of blood and enriches PBMC in 6 harvest phases with approximately 10 ml volume each. In parallel to the collection of cells, 120 ml of autologous plasma will be collected during the apheresis procedure and stored at 4° C. in a standard blood bag. During the whole apheresis procedure ACD-A (Baxter) is used as anticoagulant to prevent clotting of blood. The AutoPBSC program uses ACD-A at 0.083 ml/ml (relation 1:12), however the amount can be adapted within defined ranges (0.071-0.1 ml/ml), if necessary. At the end of the apheresis the concentration of ACD-A in the cell product and plasma is documented in the production log.

Cell Processing

All steps described here are done maintaining a closed system. In practice excipients are pre-filled in blood bags in the clean room (category A) and added to the cells by connecting the bags using a sterile tubing welder (TSCD®, Terumo). The apheresate is transferred to a standard blood bag (Compoflex P1461 500 ml, Fresenius) by welding the tubes of the bags with the TSCD®. A small retention sample is maintained in the original blood bag that will be used for counting of cells after bags have been separated using a portable tubing sealer (Fresenius NBPI). Next, cells are separated from plasma by centrifugation at 300×g for 15 min at room temperature (RT). Plasma is removed from the bag by pressing it to a sterile connected empty bag, using a plasma extractor (Baxter). The bags are separated by a portable tubing sealer. To lyse erythrocytes the bag containing the erythrocyte lysing buffer (ACK) is connected by the TSCD and the cell pellet is resuspended in 200 ml erythrocyte lysis buffer and incubated for 15 min, RT, shaking (3 rpm) on a wave platform shaker (Heidolph). At the end of the incubation period cells are washed with 200 ml CPD 12.6%/saline and centrifuged for 15 min at 200 g at 4° C. Supernatant is removed from the bag by pressing it to a empty bag, using a plasma extractor. The cells are washed again with 200 ml CPD 12.6%/saline. Cells are centrifuged for 15 min at 200 g at 4° C. and supernatant is removed from the bag. Cells are transferred to a 150 ml bag (Compoflex 1459, Fresenius) and a retention sample is taken for cell counting. $1.5-2\times10^9$ PBMC will be re-suspended in 10 ml saline and 1 ml peptide-pool solution containing 0.5 mg/ml of each GMP manufactured peptide added. The selected peptides (e.g. MBP1, MBP2, MBP3, MBP4, PLP1, MOG1 and MOG2) will be used for coupling. The coupling reaction is initiated by the addition of 1 ml of 100 mg/ml of freshly prepared water-soluble 1-ethyl-3-(3-dimethylaminopropyl)-carbodiimide (EDC). Following 1 h incubation shaking at 4° C., the peptide-coupled cells are washed 2 times with 100 ml CPD/saline and finally re-suspended in autologous plasma at a concentration given by the specification ($1\times10^5$, $1\times10^6$ or $1\times10^7$ cells/ml). At this time sample is taken for release testing prior to infusion. Cells will be carefully checked for the absence of clumping. 100 ml of final ETIMS cell product will be infused using a standard blood transfusion kit with inline-filter (200 μm). The control of critical steps and intermediates are described in IMPD 2.2.P.3.4 and the flow chart (IMPD Figures 2.1.P.3.3 1-3).

The whole manufacture process is performed within standard blood bags in a functionally closed system. In practice peptides, lysis buffer and washing solutions are filled in standard blood bags under sterile and endotoxin free conditions in a licensed clean room laboratory (category A, ISO14644 certified)) following strict GMP standards at Department of Transfusion Medicine. In the manufacture process the addition of these materials/reagents are carried out by welding the tubes of the respective blood bags with a sterile tubing welder (Terumo TSCD®).

The most preferred coupling agent for the process described above is by 1-ethyl-3-(3-dimethylaminopropyl)-carbodiimide (ECDI) as described above. However, other coupling agents (e.g. based on different carbodiimides) do qualify as well.

Further aspect of the invention therefore are:
17) A process for the manufacture of a peripheral blood mononuclear coupled with at least five of the following eight immunodominant myelin peptides:
MBP 13-32, MBP 83-99, MBP 111-129, MBP 146-170, PLP 139-154, MOG 1-20, MOG 35-55 and MBP 82-98,
containing the steps of isolating peripheral blood mononuclear cells, adding the selected peptides and subsequent adding of the coupling agent.
18) A process for the manufacture of a peripheral blood mononuclear coupled with six or seven or eight of the following eight immunodominant myelin peptides:
MBP 13-32, MBP 83-99, MBP 111-129, MBP 146-170, PLP 139-154, MOG 1-20, MOG 35-55 and MBP 82-98,
containing the steps of isolating peripheral blood mononuclear cells, adding the selected peptides and subsequent adding of the coupling agent.
19) A process for the manufacture of a peripheral blood mononuclear coupled with at least five of the following eight immunodominant myelin peptides:
MBP 13-32, MBP 83-99, MBP 111-129, MBP 146-170, PLP 139-154, MOG 1-20, MOG 35-55 and MBP 82-98,
in which the coupling agent is ECDI.

It has to be understood that in any of the aspects 17-19 described above the blood cells may be autologous or allogeneic.

Validation of the Manufacture Process

Validation of Infrastructure and Technical Equipment

Several validation runs are to be performed to assure that the infrastructure and the technical equipment are suitable for the manufacture process. The collection of cells will be performed in a apheresis unit such as the Department for Transfusion Medicine, UKE (see also Validation of leukapheresis) following SOPs. Cells will be processed in a Clean room. Washing, centrifugation and incubation steps will be done in a clean room Category D (Room 29) while maintaining a closed system. The system will be opened only in the clean room category A. All procedures will be performed by trained personnel only.

All technical equipment used for the processing of cells is certified for its intended use and maintained following SOP's. Only material that has passed the Quality control will be used.

Validation of Leukapheresis

Validation of the apheresis protocol and the characterisation of the cell product were done with aphereses from healthy donors and MS patients. All Aphereses were run on a CobeSpectra apheresis machine at the Department for Transfusion Medicine, UKE. The AutoPBSC program has been selected for several reasons (Table 1). 1) By processing a standardized blood volume (4500 ml) we obtained a sufficient yield of cells. 2) The cell product has a high purity of mononuclear cells in a standardized volume of the cell product. 3) Compared to the manual program the erythrocyte count is lower.

TABLE 1

| Apheresis | Duration (min) | Blood Volume (ml) of patient | Product Volume (ml) | PBMC $\times10^9$ | % lymphocytes (within MNC) | % monocytess (within MNC) |
|---|---|---|---|---|---|---|
| 290SA | 128 | 4500 | 61 | 5.5 | 77.6 | 17.8 |
| IJ1804 | 86 | 4552 | 61 | 5.1 | 80.2 | 13.4 |
| 445CO | 88 | 3908 | 61 | 5.5 | 67.7 | 15.2 |
| 978TH | 99 | 5502 | 61 | 5.5 | 62.4 | 21.5 |
| RM1401 | 102 | 5153 | 60 | 4.2 | 71.0 | 22.8 |
| IJ2801 | 115 | 5747 | 60 | 2.7 | 82.6 | 10.8 |
| 1066ST | 112 | 3479 | 61 | 5.5 | 72.9 | 16.7 |

Validation of Erythrocyte Lysis

Although the apheresis product contains a very low number of erythrocytes, in absolute numbers erythrocytes outweigh mononuclear cells 10 to 40 times. Thus it is necessary to lyse erythrocytes to obtain a higher purity of the cell product. For the lysis of erythrocytes we use an established lysis buffer (ACK-buffer). We tested the efficiency of the lysis buffer in buffy coats, which contain a much higher amount of erythrocytes compared to apheresate. In buffy coat we achieve efficient lysis of erythrocytes (mean hemoglobin (Hb) before lysis 10.03 g/dl, after lysis 0.63 g/dl; Table 2). In aphereses the content of erythrocytes is much lower from the beginning and is below measurable values after lysis.

TABLE 2

| Product | Hb before lysis (g/dl) | Hb after lysis (g/dl) |
|---|---|---|
| BC9198169 | 8.4 | 0.4 |
| BC9204876 | 12.6 | 1.0 |

TABLE 2-continued

| Product | Hb before lysis (g/dl) | Hb after lysis (g/dl) |
|---|---|---|
| BC9247719 | 9.8 | 0.5 |
| BC9261124 | 9.32 | 0.6 |

Filling of Blood Bags in Clean Room

All reagents will be filled through a sterile tube which has a Luer-lock device. The tube will be welded to the bag using a sterile welding device. After the reagents have been filled in the bag, the tube will be separated using a portable tubing sealer.

Cell Number

The absolute cell number in the product is a critical point in the manufacture process. During the manufacture process cells are lost (Table 3). Thus it is essential to define minimal cell numbers that are required for the production of the ETIMS product. These cell numbers have to be checked through in-process controls. The acceptance criteria for the cell numbers necessary for the manufacture process have been defined in several validation runs using buffy coats. The cell content of buffy coat is approximately $1 \times 10^9$ cells, thus for the validation runs a final cell number of $5 \times 10^8$ cells was targeted. Cell counts were assessed before starting the manufacture process, before the coupling reaction and after the last washing step. In all validation runs the target cell count could be reached, when the initial cell number was higher than $1.2 \times 10^9$.

TABLE 3

| Buffy coat | Duration (min) | Initial Cell count | Cell count after lysis | Cell count after coupling |
|---|---|---|---|---|
| 9261124 | 320 | $16.5 \times 10^8$ | $9.95 \times 10^8$ | $7.2 \times 10^8$ |
| 9247719 | 330 | $17 \times 10^8$ | $11 \times 10^8$ | $6.5 \times 10^8$ |
| 9204876 | 380 | $15 \times 10^8$ | $11.4 \times 10^8$ | $10 \times 10^8$ |
| 9198169 | 350 | $12 \times 10^8$ | $8.6 \times 10^8$ | $11 \times 10^8$ |

Duration of Manufacture Process

We aimed at reducing the duration of the manufacture process in order to enhance viability and lower the risk of microbiological contamination. Since in several validation runs residual amounts of EDC could not be detected in the first washing solution after the coupling reaction, we reduced a washing step after the lysis of erythrocytes and one after the coupling reaction. This led to a reduction of the manufacture process of approximately 57 minutes. The reduction of the duration of the manufacture process was paralleled by an increase in cell viability measured as membrane integrity by FACS-Analysis (Ph Eur 2.7.29). The mean duration is 292 min (Table 4).

TABLE 4

| Product | Duration (min) | Initial Cell count | Cell count after lysis | Cell count after coupling |
|---|---|---|---|---|
| RM1401 | 295 | $2 \times 10^9$ | $1.4 \times 10^9$ | $1.2 \times 10^9$ |
| IJ2801 | 295 | $2.5 \times 10^9$ | $2.2 \times 10^9$ | $1.8 \times 10^9$ |
| 9373085 | 285 | $1.3 \times 10^9$ | $1.0 \times 10^9$ | $0.8 \times 10^9$ | pH

The mean pH in the product after resuspension in human plasma was pH 7.7 (range 7.6-7.8; n=8). We used autologous plasma in validation runs with apheresate and third party plasma matched for blood group in validation runs with buffy coat. pH was measured in supernatants of washing steps. The pH of lysis buffer is pH 7.4 the pH of the CPD buffer is pH 5.8.

Viability

Cell viability was assessed by measuring membrane integrity by Trypan blue exclusion and FACS (Ph. Eur. 2.7.29) at different time-points and storage conditions. (see IMPD 2.1.P.8).

Peptide Binding

The objective of the study was to evaluate whether we achieve efficient coupling of peptides to the surface of PBMC in the manufacture process in bags.

In-vitro we have demonstrated that the presence of both EDC and peptide is necessary for efficient binding of peptide to the cell surface (Figure 2.1.P.3.5-1). To assess the efficiency of the coupling reaction in the manufacture process in bags, one of the seven peptides (PLP139-154) has been replaced by a biotinylated peptide (biotinPLP139-154). Binding of the peptide to the surface of the cells has been detected by FACS and fluorescence microscopy using fluorophore conjugated streptavidin (Streptavidin-Cy3 and Streptavidin-APC respectively). In the study we demonstrate in 2 separate validation runs that the peptide is binding efficiently to the surface of PBMC during the manufacture process in bags. One result representative of 2 independent validation runs is for example shown in FIG. 1.

Since the volume for the coupling reaction might vary (target volume 10 ml) we assessed the efficiency of the coupling procedure in 4 different volumes. At a concentration ranging for PBMC: $1 \times 10^7$-$0.33 \times 10^7$ cells/ml; for EDC: 100 mg/ml-33 mg/ml and for peptide-pool at 0.05 mg/ml-0.017 mg/ml peptide the binding is efficient. Further reduction of the concentration reduces the binding efficiency below accepted levels. Thus a volume range of 10-20 ml for the coupling procedure is acceptable.

Sterility

Sterility was maintained in 5 independent validation runs. Samples were tested for aerobial and anaerobial bacteria and fungi.

Endotoxin

Final washing solutions of 3 validation runs were tested for the presence of endotoxins (Pyrogene®, Lonza). We could not detect endotoxin (<0.5 EU/ml) in the supernatant of the last washing solution before resuspension of cells in autologous plasma. The presence of endotoxins cannot be assessed in human plasma, since plasma inhibits the test.

Aggregates

Several measures were taken to ensure against the presence of aggregates.

a) We did not see aggregates by visual inspection in any of the products in the validation runs (n=14). We simulated the infusion on the bench with the blood transfusion kit with an inline filter (200 μm) that will be used for patients. We did not see aggregates in the filter after having passed the cells. To further ensure against aggregates we counted the cell concentration before and after having passed through the filter and could not see any difference (n=2).

b) We assessed the presence of aggregates by microscopy in a blood smear or after transferring cells to a cell culture plate. We did not see a difference compared to non-treated cells.

c) In order to detect and quantify micro-aggregates we analysed several products (n=5) by FACS. By assessing the forward scatter area (FSC-A) and the forward scatter width (FSC-W) we could not detect a higher frequency of micro-aggregates in the cell product compared to the cells before EDC treatment. The frequency of aggregates did not increase during the storage period of 4 h.

d) Injection of human product (ETIMS) in mice (n=20) did not lead to embolism, because of aggregates in any of the mice.

Identity

We analyzed the cellular composition of the apheresate and the final drug product, with the objective to evaluate differences in the final cellular composition of the drug product resulting from the processing of the cells. A clear phenotypic characterisation of the final product is hampered by the treatment of the cells, most probably because the chemical treatment alters the target structure for the specific antibodies. We will thus phenotype the cell product before the processing of the cells in order to assess whether the relation between different populations (T cells, B cells, monocytes) have an influence on the treatment outcome. The aim is to establish acceptance criteria for the further development of the drug product.

Pre-Clinical Safety

Animal studies: Two different experimental settings were used for the assessment of toxicity. 1) Toxicologic testing of the human product can only be assessed in the short term because of immunotoxicity when tested in different species. Thus we assessed short term toxicity of the human product in immune-compromised mice (severe combined immunodeficiency; SCID). 2) Mid-term toxicity of syngeneic splenocytes coupled with the seven myelin peptides used in the trial was assessed in the SJL model.

Both toxicologic studies were conducted by LPT Laboratory of Pharmacology and Toxicology GmbH & Co. KG, Redderweg, Hamburg, a GLP-certified laboratory.

Acute Toxicity Study of Human Peptide-Coupled Peripheral Blood Mononuclear Cells (PBMC) and Human Plasma by Single Intravenous Administration to SCID Mice (LPT 22043).

| Test item | $1 \times 10^9$ Human PBMC chemically coupled to seven myelin peptides (MBP13-32 (MBP1), MBP83-99 (MBP2), MBP111-129 (MBP3), MBP146-170 (MBP4), MOG1-20 (MOG1), MOG35-55 (MOG2), PLP139-154 PLP1) resuspended in 100 ml human plasma. Human plasma served as control |
|---|---|
| Number of experiments | Two different, at two independent time-points, manufactured human peptide-coupled PBMC (Product A and Product B) |
| Number of animals per experiment | 5 males and 5 females received peptide-coupled cells, 1 male and 1 female received human plasma as control |
| Intravenous injection | Dose/approx. 15 seconds |
| Administration volume | 200 µl i.v. |
| Dose | $2 \times 10^6$ peptide-coupled human PBMC |
| Body weight (at start of treatment) | |
| Males: | 17-22 g |
| Females: | 15-17 g |
| Age (at start of treatment) | |
| Males: | 41-48 days |
| Females: | 41-48 days |
| Identification of animal | By coloured marks and cage label |
| Duration of experiment | At least 5 adaptation days<br>1 test day<br>24 hours recovery period |
| Evaluation | Observations were performed for all animals and recorded systematically (with individual records being maintained for each animal) before and immediately, 5, 15, 30 and 60 min, as well as 3, 6 and 24 hours after administration. |
| Observation | Changes of skin and fur, eyes and mucous membranes, respiratory and circulatory function, autonomic and central nervous system and somatomotor activity as well as behaviour pattern were observed. |
| Measurements | Individual body weights were recorded before administration of the test item and after 24 hours. Changes in weight were calculated and recorded. At the end of the experiments all animals were sacrificed under ether anaesthesesia by cutting the aorta abdominalis, exsanguinated, weighed, dissected and inspected macroscopically under the direction of a pathologist. |

Summarized Results

Under the present test conditions, single intravenous injections of 200 µL Human peptide-coupled peripheral PBMC (Product A), human peptide-coupled PBMC (Product B) or human plasma to mice did not lead to any signs of toxicity. No mortality occurred.

| | Product A | | Product B | | Human Plasma | |
|---|---|---|---|---|---|---|
| Symptoms/Criteria | males | females | males | females | males | females |
| Clinical signs | none | none | none | none | none | none |
| mortality within 6 h | 0 | 0 | 0 | 0 | 0 | 0 |
| within 24 h | 0 | 0 | 0 | 0 | 0 | 0 |
| Mean body weight start | 18.6 | 15.6 | 20.4 | 16.2 | 20.5 | 17.0 |
| after 24 h | 19.0 | 15.8 | 20.6 | 16.4 | 20.5 | 17.5 |
| Inhibition of body weight gain | none | none | none | none | none | none |
| Necropsy findings * | none | 2 of 5 | 4 of 5 | 4 of 5 | 2 of 2 | 2 of 2 |

| | Product A | | Product B | | Human Plasma | |
|---|---|---|---|---|---|---|
| Symptoms/Criteria | males | females | males | females | males | females |

* A reduced spleen size was observed in 0 of 5 male and 2 of 5 female animals treated with Product A, 4 of 5 male and 4 of 5 female animals treated with Product B and 2 of 2 male and 2 of 2 female animals treated with human plasma.

Acute Toxicity Study of Peptide Coupled Splenocytes by Single Intravenous Administration to SJL Mice (LPT 21988)

| Test item | Syngeneic splenocytes chemically coupled to seven myelin peptides (MBP13-32 (MBP1), MBP83-99 (MBP2), MBP111-129 (MBP3), MBP146-170 (MBP4), MOG1-20 (MOG1), MOG35-55 (MOG2), PLP139-154 (PLP1)) resuspended in PBS. |
|---|---|
| Number of experiments | 1 |
| Number of animals per experiment | 5 males and 5 females received peptide-coupled splenocytes |
| Intravenous injection | Dose/approx. 15 seconds |
| Administration volume | 200 μl iv. |
| Dose | $5 \times 10^7$ peptide-coupled splenocytes |
| Body weight (at start of treatment) | |
| Males: | 17-19 g |
| Females: | 17-18 g |
| Age (at start of treatment) | |
| Males: | 43 days |
| Females: | 43 days |
| Identification of animal | By coloured marks and cage label |
| Duration of experiment | At least 5 adaptation days<br>1 test day<br>2 recovery weeks |
| Evaluation | Observations were performed for all animals and recorded systematically (with individual records being maintained for each animal) before and immediately, 5, 15, 30 and 60 min, as well as 3, 6 and 24 hours after administration. All animals were observed for a period of 14 days. |
| Observation | Changes of skin and fur, eyes and mucous membranes, respiratory and circulatory function, autonomic and central nervous system and somatomotor activity as well as behaviour pattern were observed. |
| Measurements | Individual body weights were recorded before administration of the test item and thereafter every day for the first three days followed by weekly intervals up to the end of the study. Changes in weight were calculated and recorded.<br>At the end of the experiments all animals were sacrificed under ether anaesthesia by cutting the aorta abdominalis, exsanguinated, weighed, dissected and inspected macroscopically under the direction of a pathologist. |

Summarized Results

Under the present test conditions, a single intravenous injection of $5 \times 10^7$ peptide-coupled splenocytes to mice did not lead to any signs of toxicity. No mortality occurred. All animals gained the expected body weight throughout the whole study period.

| | | $5 \times 10^7$ cells/animal iv.<br>n = 5 | |
|---|---|---|---|
| Symptoms/Criteria | | males | females |
| Clinical signs | | none | none |
| mortality | within 6 h | 0 | 0 |
| | within 24 h | 0 | 0 |
| | within 7 d | 0 | 0 |
| | within 14 d | 0 | 0 |
| Mean body weight | start | 18.2 | 17.6 |
| | after 7 d | 19.8 (+8.8) | 18.4 (+29.2) |
| | after 14 d | 22.4 (+23.1) | 20.6 (+37.8) |
| Inhibition of body weight gain | | none | none |
| Necropsy findings | | none | none |

D = days
H = hours
In brackets: body weight gain in %, compared with the start value
i.v. = intravenous

In-Vitro Analysis with Human Cells:

The treatment is only administered once to patients and is being administered by the tolerogenic iv. route with cells undergoing apoptosis. Thus there is little concern that a cytotoxic/anaphylactic response will be induced following administration of cells. We test a possible reaction between treated cells and T cells from recipient patient in-vitro by a mixed lymphocyte reaction prior to the study in healthy donors and MS patients. These assays document proliferation as well as cytokine release.

Proliferation assays against the antigen used in the trial will generate short term TCL. These antigen-specific T cells are co-cultured with autologous ECDI fixed antigen coupled APC in a 24 well culture plate at 37° C. in 5% $CO_2$ at a ratio of 1:1 to 1:2 (T:APC) with total $2-4 \times 10^6$ total mixed cells. After 24 h cultured cell mixtures are collected and applied to a Ficoll gradient to isolate viable cells. After washing in culture medium (RPMI 1640) live cells are remixed with antigen in the presence of APC and evaluated for proliferation, activation status by FACS, cytokine secretion (IL-2, IL-4, IFN-g, IL-17) and cytokine mRNA expression. Depending on the timing of restimulation, one might expect anergy induction and/or induction of activation-induced cell death (AICD). Such cases should be properly documented.

The objective of this study was to evaluate the effect of peptide-coupled PBMC on immune activation of PBMC in-vitro. PBMC from MS patients (n=2) and a healthy control were cultured in the presence of peptide-coupled PBMC and analysed for proliferation response by thymidine incorporation and cytokine secretion (IL12, IFN-γ, IL10, IL1β, TNF-α) using a FACS based array (FlowCytomix, Bendermedsystems).

To assess cell proliferation in response to peptide-coupled cells, PBMC were seeded in two 96 well plates at $1 \times 10^5$ cells/well in complete IMDM containing 100 U/ml penicillin/streptomycin, 50 µg/ml gentamicin, 2 mM L-glutamine, 5% heat decomplemented human serum. To the respective wells we added either $5 \times 10^4$ PBMC treated with EDC in the presence of the 7 peptides used in the trial (=peptide-coupled PBMC, tAPCpep), $5 \times 10^4$ PBMC treated with EDC but without peptide (tAPC), 2.5 µg/ml phytohhaemagglutinin (PHA) or without further stimulus (APC).

Presence of peptide-coupled cells did not induce proliferation in PBMC compared to unstimulated PBMC or PHA stimulated PBMC (FIG. 3).

We also analyzed for the presence of inflammatory cytokines after 3 h and 24 h. Briefly, PBMC were cultured over night in complete IMDM containing 100 U/ml penicillin/streptomycin, 50 µg/ml gentamicin, 2 mM L-glutamine, 5% heat decomplemented human serum, either in the presence of 2.5 µg/ml PHA or without stimulus. After 24 h, cells were washed in complete IMDM and seeded in a 24 well plate ($4 \times 10^6$/ml) in the presence of either PBMC treated with EDC and 7 peptides used in the trial (=peptide-coupled PBMC, tAPCpep), $1 \times 10^6$ PBMC treated with EDC but without peptide (tAPC), 2.5 µg/ml PHA (PHA) or without further stimulus (APC).

Figure 4:
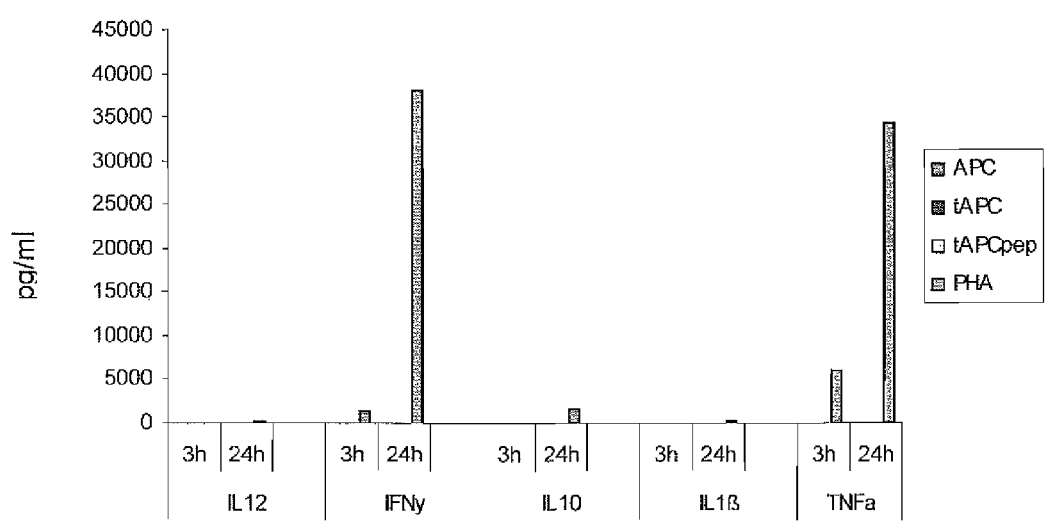
Figure 5:
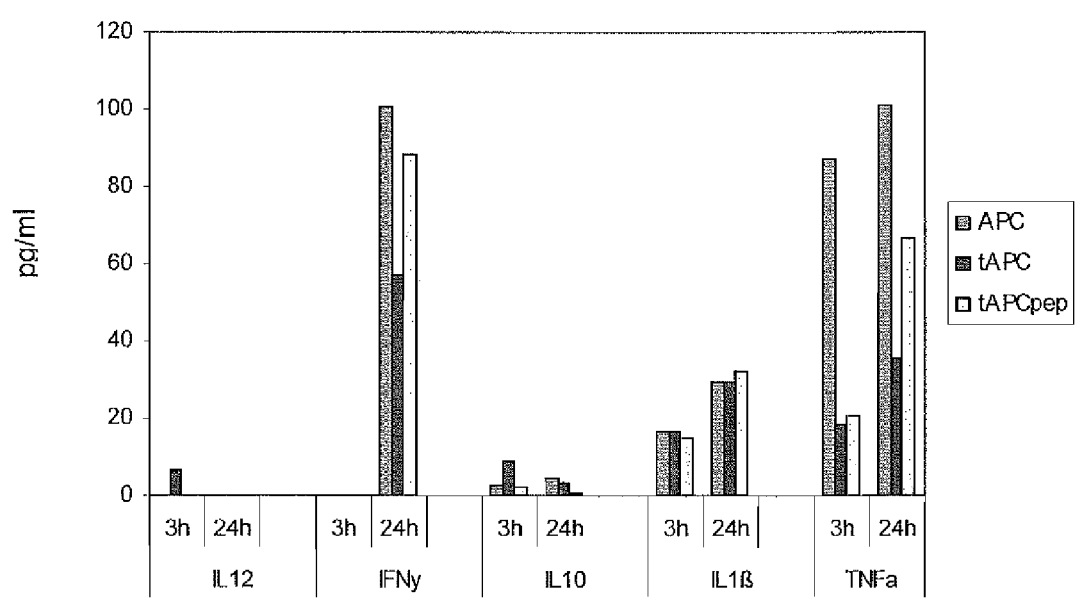

As depicted in FIG. 4 and FIG. 5 there is no significant induction of inflammatory cytokines in the presence of peptide-coupled PBMC compared to the negative control (APC).

Depicted in FIG. 5 are the concentrations of cytokines without PHA control.

Figure 6:
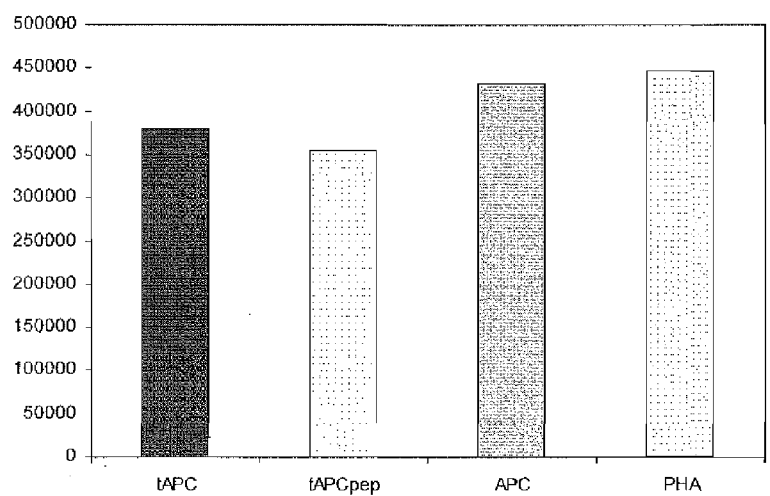
Figure 7:
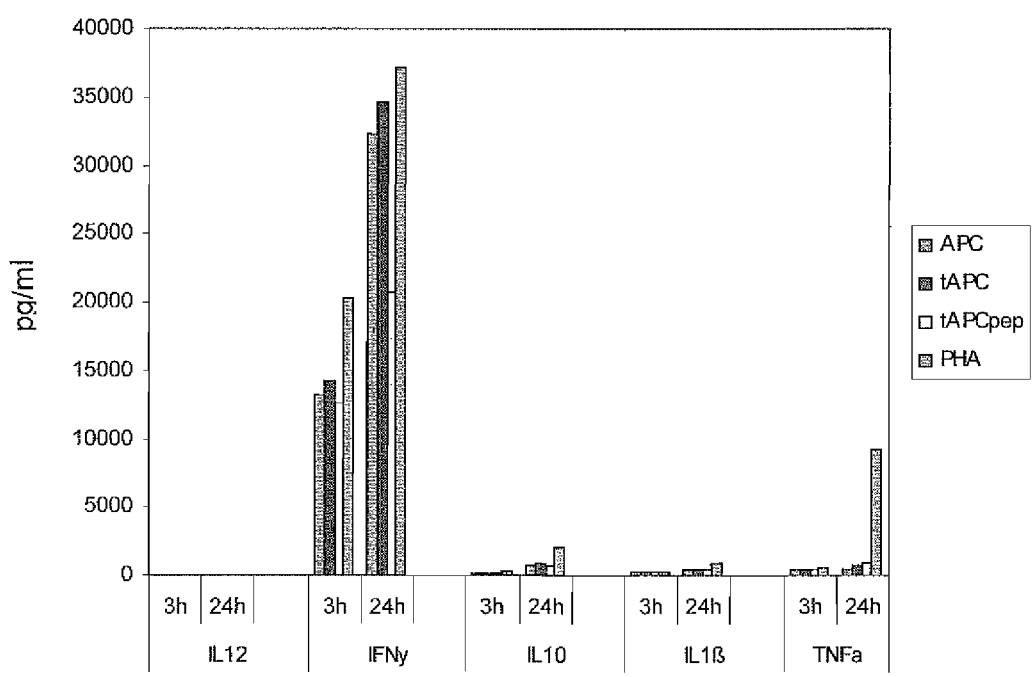

To analyze whether the response to peptide coupled cells differs dependent on the activation status of the cells we pre-activated PBMC with PHA for 24 h and added the peptide-coupled PBMC. We did not see any induction of proliferation (FIG. 6) or cytokines (FIG. 7) in response to peptide-coupled cells.

In summary we did not see any activation of immune cells induced by the presence of peptide-coupled cells in-vitro. This result correlates well with the experience that we and others (34) have made with tolerization of human T-cell clones in-vitro and the induction of tolerance with peptide-coupled cells in-vivo in different animal models.

Potency of Human Peptide Coupled Cells In-Vitro

Figure 8:
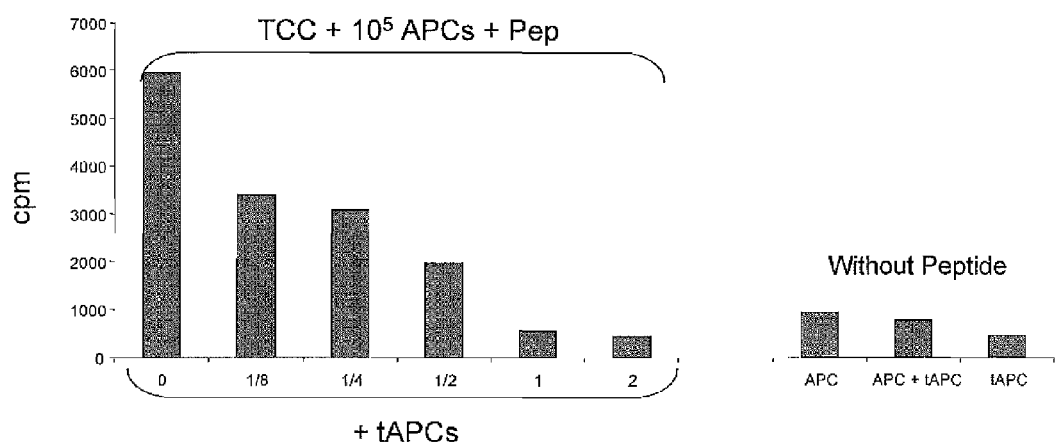

The objective of the study was to evaluate the effect of peptide-coupled cells on the antigen-specific response of human T cells. We used a T-cell clone (TCC) obtained from the cerebrospinal fluid (CSF) of an MS patient during relapse. Briefly, TCC ($2 \times 10^4$ cells/well) was cultured in complete IMDM (containing 100 U/ml penicillin/streptomycin, 50 µg/ml gentamicin, 2 mM L-gutamine, 5% heat decomplemented human serum) and pulsed with the peptide (MSI118) in the presence of irradiated PBMC ($1 \times 10^5$ cells/well). Peptide. (MSI118, 10 µg/ml) coupled PBMC were added to the wells at different cell concentrations. Proliferative response of the TCC was measured by $^3$H-Thymidine incorporation after 72 h (FIG. 8).

Incubation of TCC with the specific peptide in the presence of antigen-coupled cells reduces the antigen specific response measured by thymidine incorporation in a dose-dependent manner.

Figure 9:
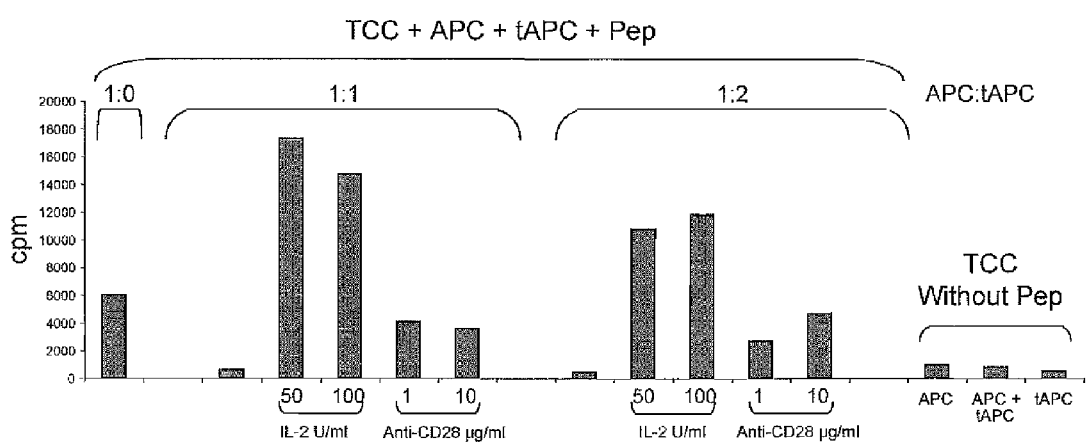

To exclude a toxic inhibition of the peptide-coupled cells on the TCC we added IL-2 or anti-CD28 monoclonal antibody to respective wells. As depicted in FIG. 9, proliferation of the TCC can be recuperated by the addition of either IL-2 or the anti-CD28 antibody in the presence of peptide-coupled cells.

It has been suggested that by fixing peptide pulsed antigen presenting cells a immunologic synapse cannot be formed and anergy is induced in autoreactive T cells through presentation of the peptide through the MHC without co-stimulation. The immunologic synapse refers to the spatially organized motif of membrane proteins and cytosolic molecules that forms at the junction between T cell and an antigen presenting cell.

To further explore the invention we analyze the formation of the immunologic synapse by fluorescence microscopy and by analysing the biophysical parameters (eg. calcium influx) characterizing TCR MHC interaction.

Until now it is not clear from the literature, neither from the animal model, nor human studies, which subset of antigen presenting cells is most important in the tolerization process. We examine this question by analyzing the potency of the regimen as described above, after isolating specific cells from the PBMC population. Isolation of cells are performed using columns with labelled beads or a cell sorter.

Definition of Myelin Peptides

The myelin peptides specifically disclosed in this application are characterized by the following sequences:

```
MBP 13-32
(Seq ID 01): KYLATASTMDHARHGFLPRH

MBP 83-99
(Seq ID 02): ENPVVHFFKNIVTPRTP

MBP 111-129
(Seq ID 03): LSRFSWGAEGQRPGFGYGG

MBP 111-129
(Seq ID 04): AQGTLSKIFKLGGRDSRSGSPMARR

PLP 139-154
(Seq ID 05): HCLGKWLGHPDKFVGI

MOG 1-20
(Seq ID 06): GQFRVIGPRHPIRALVGDEV

MOG 35-55
(Seq ID 07): MEVGWYRPPFSRVVHLYRNGK

MBP 82-98
(Seq ID 08): DENPVVHFFKNIVTPRT
```

The sequences defined above include different end modifications of the peptides, e.g. acetylation, amidation, carboxylation.

EXAMPLE $1.5-2 \times 10^9$ peripheral blood mononuclear cells are isolated from a MS patient. The isolated cells are coupled according to the manufacture process described above with a cocktail of the following peptides MBP 13-32, MBP 83-99, MBP 111-129, MBP 146-170, PLP 139-154, MOG 1-20 and MOG 35-55. The resulting suspension of approximately $10^9$ cells suspended in 100 ml water buffered to pH 7.2-7.8 is infused intravenously to the patient. MRI examinations carried out before and after application (e.g. 1 day, 1 week, 1 month, 6 months, 1 year after application) convincingly demonstrates the efficacy of the procedure in terms of reduction of CNS-inflammation. The MRI findings are in line with other clinical symptoms.

It will be appreciated by the expert skilled in the art that the description relating to the manufacturing process (including all tests and validation steps) are provided as examples. They are not meant to limit the invention in any way. The expert skilled in the art will certainly be able to carry out the invention as described above but also to modify the invention in various aspects based on his general knowledge without any need to be inventive.

LITERATURE REFERENCES

1. Miller, S. D., D. M. Turley, and J. R. Podojil. 2007. Antigen-specific tolerance strategies for the prevention and treatment of autoimmune disease. *Nat Rev Immunol* 7:665.
2. Bielekova, B., M. H. Sung, N. Kadom, R. Simon, H. McFarland, and R. Martin. 2004. Expansion and functional relevance of high-avidity myelinspecific CD4+ T cells in multiple sclerosis. *J Immunol* 172:3893.
3. Pope, L., P. Y. Paterson, and S. D. Miller. 1992. Antigen-specific inhibition of the adoptive transfer of experimental autoimmune encephalomyelitis in Lewis rats. *J Neuroimmunol* 37:177.
4. Bielekova, B., B. Goodwin, N. Richert, I. Cortese, T. Kondo, G. Afshar, B. Gran, J. Eaton, J. Antel, J. A. Frank, H. F. McFarland, and R. Martin. 2000. Encephalitogenic potential of the myelin basic protein peptide (amino acids 83-99) in multiple sclerosis: results of a phase II clinical trial with an altered peptide ligand. *Nat Med* 6:1167
5. Krogsgaard, M., K. W. Wucherpfennig, B. Cannella, B. E. Hansen, A. Svejgaard, J. Pyrdol, H. Ditzel, C. Raine, J. Engberg, and L. Fugger. 2000. Visualization of myelin basic protein (MBP) T cell epitopes in multiple sclerosis lesions using a monoclonal antibody specific for the human histocompatibility leukocyte antigen (HLA)-DR2-MBP 85-99 complex. *J Exp Med* 191:1395.
6. Warren, K. G., I. Catz, L. Z. Ferenczi, and M. J. Krantz. 2006. Intravenous synthetic peptide MBP82-98 delayed disease progression in an HLA Class II defined cohort of patients with progressive multiple sclerosis: results of a 24-month double-blind placebo-controlled clinical trial and 5 years of follow-up treatment. *Eur J Neurol* 13:887.
7. Warren, K. G., I. Catz, and K. W. Wucherpfennig. 1997. Tolerance induction to myelin basic protein by intravenous synthetic peptides containing epitope P85 VVH-FFKNIVTP96 (SEQ ID NO: 9) in chronic progressive multiple sclerosis. *J Neurol Sci* 152:31.
8. Beuvery, E. C., G. J. Speijers, B. I. Lutz, D. Freudenthal, V. Kanhai, B. Haagmans, and H. J. Derks. 1986. Analytical, toxicological and immunological consequences of the use of N-ethyl-N'-(3-dimethylaminopropyl) carbodiimide as coupling reagent for the preparation of meningococcal group C polysaccharide-tetanus toxoid conjugate as vaccine or human use. *Dev Biol Stand* 63:117.
9. Drager, L. J., U. Julius, K. Kraenzle, J. Schaper, M. Toepfer, K. Zygan, V. Otto, and E. Steinhagen-Thiessen. 1998. DALI—the first human whole-blood low-density lipoprotein and lipoprotein (a) apheresis system in clinical use: procedure and clinical results. *Eur J Clin Invest* 28:994.
10. Liu, Y., L. Gan, D. J. Carlsson, P. Fagerholm, N. Lagali, M. A. Watsky, R. Munger, W. G. Hodge, D. Priest, and M. Griffith. 2006. A simple, crosslinked collagen tissue substitute for corneal implantation. *Invest Opthalmol Vis Sci* 47:1869.
11. Moshnikova, A. B., V. N. Afanasyev, O. V. Proussakova, S. Chemyshov, V. Gogvadze, and I. P. Beletsky. 2006. Cytotoxic activity of 1-ethyl-3-(3-dimethylaminopropyl)-carbodiimide is underlain by DNA interchain crosslinking. *Cell Mol Life Sci* 63:229.
12. Schneerson, R., O. Barrera, A. Sutton, and J. B. Robbins. 1980. Preparation, characterization, and immunogenicity of *Haemophilus influenzae* type b polysaccharide-protein conjugates. *J Exp Med* 152:361.
13. Tai, J. Y., P. P. Vella, A. A. McLean, A. F. Woodhour, W. J. McAleer, A. Sha, C. Dennis-Sykes, and M. R. Hilleman. 1987. *Haemophilus influenzae* type b polysaccharide-protein conjugate vaccine. *Proc Soc Exp Biol Med* 184:154.
14. Wilchek, M., T. Miron, and J. Kohn. 1981. A highly sensitive colorimetric method for the determination of carbodiimides. *Anal Biochem* 114:419.
15. Miller, S. D., R. P. Wetzig, and H. N. Claman. 1979. The induction of cellmediated immunity and tolerance with protein antigens coupled to syngeneic lymphoid cells. *J Exp Med* 149:758.
16. Kennedy, M. K., M. C. Dal Canto, J. L. Trotter, and S. D. Miller. 1988. Specific immune regulation of chronic-relapsing experimental allergic encephalomyelitis in mice. *J Immunol* 141:2986.
17. Tan, L. J., M. K. Kennedy, M. C. Dal Canto, and S. D. Miller. 1991. Successful treatment of paralytic relapses in adoptive experimental autoimmune encephalomyelitis via neuroantigen-specific tolerance. *J Immunol* 147:1797.
18. Vandenbark, A. A., M. Vainiene, K. Ariail, S. D. Miller, and H. Offner. 1996. Prevention and treatment of relapsing autoimmune encephalomyelitis with myelin peptide-coupled splenocytes. *J Neurosci Res* 45:430.
19. Karpus, W. J., J. G. Pope, J. D. Peterson, M. C. Dal Canto, and S. D. Miller. 1995. Inhibition of Theiler's virus-mediated demyelination by peripheral immune tolerance induction. *J Immunol* 155:947.
20. Miller, S. D., B. L. McRae, C. L. Vanderlugt, K. M. Nikcevich, J. G. Pope, L. Pope, and W. J. Karpus. 1995. Evolution of the T-cell repertoire during the course of experimental immune-mediated demyelinating diseases. *Immunol Rev* 144:225.
21. Jenkins, M. K., and R. H. Schwartz. 1987. Antigen presentation by chemically modified splenocytes induces antigen-specific T cell unresponsiveness in vitro and in vivo. *J Exp Med* 165:302.
22. Turley, D. M., and S. D. Miller. 2007. Peripheral tolerance induction using ethylenecarbodiimide-fixed APCs uses both direct and indirect mechanisms of antigen presentation for prevention of experimental autoimmune encephalomyelitis. *J Immunol* 178:2212.

23. Kennedy, M. K., L. J. Tan, M. C. Dal Canto, V. K. Tuohy, Z. J. Lu, J. L. Trotter, and S. D. Miller. 1990. Inhibition of murine relapsing experimental autoimmune encephalomyelitis by immune tolerance to proteolipid protein and its encephalitogenic peptides. *J Immunol* 144:909.
24. Tan, L. J., M. K. Kennedy, and S. D. Miller. 1992. Regulation of the effector stages of experimental autoimmune encephalomyelitis via neuroantigenspecific tolerance induction. II. Fine specificity of effector T cell inhibition. *J Immunol* 148:2748.
25. Vanderlugt, C. L., K. L. Neville, K. M. Nikcevich, T. N. Eagar, J. A. Bluestone, and S. D. Miller. 2000. Pathologic role and temporal appearance of newly emerging autoepitopes in relapsing experimental autoimmune encephalomyelitis. *J Immunol* 164:670.
26. Karpus, W. J., N. W. Lukacs, B. L. McRae, R. M. Strieter, S. L. Kunkel, and S. D. Miller. 1995. An important role for the chemokine macrophage inflammatory protein-1 alpha in the pathogenesis of the T cell-mediated autoimmune disease, experimental autoimmune encephalomyelitis. *J Immunol* 155:5003.
27. Kennedy, M. K., L. J. Tan, M. C. Dal Canto, and S. D. Miller. 1990. Regulation of the effector stages of experimental autoimmune encephalomyelitis via neuroantigen-specific tolerance induction. *J Immunol* 145:117.
28. Miller, S. D., L. J. Tan, M. K. Kennedy, and M. C. Dal Canto. 1991. Specific immunoregulation of the induction and effector stages of relapsing EAE via neuroantigen-specific tolerance induction. *Ann NY Acad Sci* 636:79.
29. Smith, C. E., T. N. Eagar, J. L. Strominger, and S. D. Miller. 2005. Differential induction of IgE-mediated anaphylaxis after soluble vs. cellbound tolerogenic peptide therapy of autoimmune encephalomyelitis. *Proc Natl Acad Sci USA* 102:9595.
30. Braley-Mullen, H., J. G. Tompson, G. C. Sharp, and M. Kyriakos. 1980. Suppression of experimental autoimmune thyroiditis in guinea pigs by pre-treatment with thyroglobulin-coupled spleen cells. *Cell Immunol* 51:408.
31. Gregorian, S. K., L. Clark, E. Heber-Katz, E. P. Amento, and A. Rostami. 1993. Induction of peripheral tolerance with peptide-specific anergy in experimental autoimmune neuritis. *Cell Immunol* 150:298.
32. Dua, H. S., D. S. Gregerson, and L. A. Donoso. 1992. Inhibition of experimental autoimmune uveitis by retinal photoreceptor antigens coupled to spleen cells. *Cell Immunol* 139:292.
33. Kennedy, K. J., W. S. Smith, S. D. Miller, and W. J. Karpus. 1997. Induction of antigen-specific tolerance for the treatment of ongoing, relapsing autoimmune encephalomyelitis: a comparison between oral and peripheral tolerance. *J Immunol* 159:1036.
34. Vandenbark, A. A., D. Barnes, T. Finn, D. N. Bourdette, R. Whitham, I. Robey, J. Kaleeba, B. F. Bebo, Jr., S. D. Miller, H. Offner, and Y. K. Chou. 2000. Differential susceptibility of human T(h)1 versus T(h) 2 cells to induction of anergy and apoptosis by ECDI/antigen-coupled antigenpresenting cells. *Int Immunol* 12:57.
35. Bielekova, B., A. Lincoln, H. McFarland, and R. Martin. 2000. Therapeutic potential of phosphodiesterase-4 and -3 inhibitors in Th1-mediated autoimmune diseases. *J Immunol* 164:1117.
36. Bielekova, B., N. Richert, T. Howard, G. Blevins, S. Markovic-Plese, J. McCartin, J, A. Frank, J. Wurfel, J. Ohayon, T. A. Waldmann, H. F. McFarland, and R. Martin. 2004. Humanized anti-CD25 (daclizumab) inhibits disease activity in multiple sclerosis patients failing to respond to interferon beta. *Proc Natl Acad Sci USA* 101:8705.
37. Calabresi, P. A., N. S. Fields, H. W. Maloni, A. Hanham, J. Carlino, J. Moore, M. C. Levin, S. Dhib-Jalbut, L. R. Tranquill, H. Austin, H. F. McFarland, and M. K. Racke. 1998. Phase 1 trial of transforming growth factor beta 2 in chronic progressive MS. *Neurology* 51:289.
38. Frank, J. A., N. Richert, B. Lewis, C. Bash, T. Howard, R. Civil, R. Stone, J. Eaton, H. McFarland, and T. Leist. 2002. A pilot study of recombinant insulin-like growth factor-1 in seven multiple sderosis patients. *Mult Scler* 8:24.
39. Paty, D. W., and D. K. Li. 1993. Interferon beta-1b is effective in relapsingremitting multiple sclerosis. II. MRI analysis results of a multicenter, randomized, double-blind, placebo-controlled trial. UBC MS/MRI Study Group and the IFNB Multiple Sclerosis Study Group. *Neurology* 43:662.
40. Filippi, M., M. A. Horsfield, H. J. Ader, F. Barkhof, P. Bruzzi, A. Evans, J. A. Frank, R. I. Grossman, H. F. McFarland, P. Molyneux, D. W. Paty, J. Simon, P. S. Tofts, J. S. Wolinsky, and D. H. Miller. 1998. Guidelines for using quantitative measures of brain magnetic resonance imaging abnormalities in monitoring the treatment of multiple sclerosis. *Ann Neurol* 43:499.
41. McFarland, H. F., J. A. Frank, P. S. Albert, M. E. Smith, R. Martin, J. O. Harris, N. Patronas, H. Maloni, and D. E. McFarlin. 1992. Using gadoliniumenhanced magnetic resonance imaging lesions to monitor disease activity in multiple sclerosis. *Ann Neurol* 32:758.
42. Miller, D. H., F. Barkhof, and J. J. Nauta. 1993. Gadolinium enhancement increases the sensitivity of MRI in detecting disease activity in multiple sclerosis. *Brain* 116 (Pt 5):1077.
43. Miller, S. D., Smith, C. E. 2006. Multi-peptide coupled-cell tolerance ameliorates ongoing relapsing EAE associated with multiple pathogenic autoreactivities. *J Autoimmunity* 27:218.
44. Kohm, A. P., Turley, D. M., Miller, S. D., 2005. Targeting the TCR: T-Cell Receptor and Peptide-Specific Tolerance-Based Strategies for Restoring Self-Tolerance in CNS Autoimmune Disease. *Int Rev Immunol* 24.361.

We claim:

1. A chemically-coupled cell which is a peripheral blood mononuclear cell (PBMC) or a red blood cell (RBC) that is chemically coupled to a cocktail of peptides, which cocktail comprises at least one of the following groups of immunodominant myelin peptides:
   Group (a) consisting of $MBP_{13-32}$, $MBP_{83-99}$, $MBP_{111-129}$, $MBP_{146-170}$, $PLP_{139-154}$, $MOG_{1-20}$ and $MOG_{35-55}$;
   Group (b) consisting of $MBP_{13-32}$, $MBP_{82-98}$, $MBP_{111-129}$, $MBP_{146-170}$, $PLP_{139-154}$, $MOG_{1-20}$ and $MOG_{35-55}$;
   Group (c) consisting of $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$; or
   Group (d) consisting of $MBP_{13-32}$, $MBP_{111-129}$, $MBP_{146-170}$, $PLP_{139-154}$, $MOG_{1-20}$ and $MOG_{35-55}$.

2. The chemically-coupled cell according to claim 1, which is a red blood cell.

3. The chemically-coupled cell according to claim 1, which is a peripheral blood mononuclear cell.

4. The chemically-coupled cell according to claim 1, wherein the peptides are chemically coupled by 1-ethyl-3-(3-dimethylaminopropyl)-carbodiimide (ECDI).

5. A process for the manufacture of a chemically-coupled cell according to claim 1, comprising contacting said PBMC or RBC with at least one of said cocktail of peptides of groups (a)-(d) in the presence of a coupling agent.

6. A The process according to claim 5, wherein the coupling agent is 1-ethyl-3-(3-dimethylaminopropyl)-carbodiimide (ECDI).

7. A pharmaceutical composition comprising one or more of the chemically-coupled cells according to claim 1 and a pharmaceutically acceptable excipient.

8. A medical product comprising one or more of the chemically-coupled cells according to claim 1 and an anticoagulant.

9. A method for the therapeutic treatment of multiple sclerosis (MS) in a subject in need thereof, comprising administering into said subject a therapeutically effective amount of said chemically-coupled cells according to claim 1.

10. The method according to claim 9, wherein the cells are allogenic cells relative to said subject.

11. The method according to claim 9, wherein the cells are autologous cells relative to said subject.

12. A method for treating multiple sclerosis (MS) in a subject in need thereof, comprising administering into said subject the pharmaceutical composition according to claim 7.

13. The chemically-coupled cell according to claim 1, wherein the cocktail of peptides comprises at least one of the groups of immunodominant myelin peptides selected from:
   Group (a) consisting of $MBP_{13-32}$, $MBP_{83-99}$, $MBP_{111-129}$, $MBP_{146-170}$, $PLP_{139-154}$, $MOG_{1-20}$ and $MOG_{35-55}$; and
   Group (c) consisting of $MBP_{13-32}$, $MBP_{83-99}$, $MBP_{111-129}$, $MBP_{146-170}$, $PLP_{139-154}$, $MOG_{1-20}$, $MOG_{35-55}$ and $MBP_{82-98}$.

14. The method according to claim 9, wherein the subject is a human subject.

* * * * *